US010401297B2

(12) United States Patent
Bartko et al.

(10) Patent No.: US 10,401,297 B2
(45) Date of Patent: *Sep. 3, 2019

(54) EXPLOSIVES DETECTION USING OPTICAL SPECTROSCOPY

(71) Applicant: BATTELLE MEMORIAL INSTITUTE, Columbus, OH (US)

(72) Inventors: Andrew P. Bartko, Columbus, OH (US); Theodore J. Ronningen, Lewis Center, OH (US)

(73) Assignee: Battelle Memorial Institute, Columbus, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/991,885

(22) Filed: May 29, 2018

(65) Prior Publication Data

US 2018/0306722 A1 Oct. 25, 2018

Related U.S. Application Data

(63) Continuation of application No. 15/292,253, filed on Oct. 13, 2016, now Pat. No. 9,983,138, which is a
(Continued)

(51) Int. Cl.
*G01N 21/65* (2006.01)
*G01N 21/64* (2006.01)
(Continued)

(52) U.S. Cl.
CPC ............ *G01N 21/65* (2013.01); *G01N 21/35* (2013.01); *G01N 21/64* (2013.01); *G01N 33/227* (2013.01);
(Continued)

(58) Field of Classification Search
CPC .... G01N 21/658; G01N 21/65; G01N 21/359; G01N 33/227; G01N 35/00029;
(Continued)

(56) References Cited

U.S. PATENT DOCUMENTS 6,485,413 B1  11/2002  Boppart et al.
6,610,977 B2  8/2003  Megerle
(Continued)

FOREIGN PATENT DOCUMENTS

EP  2133689 A1  12/2009
JP  2005091343 A  4/2005
WO  2007092009 A2  8/2007

OTHER PUBLICATIONS

Notification of Transmittal with the International Search Report and the Written Opinion of the International Searching Authority for International PCT Application No. PCT/US2015/026302; European Patent Office; Rijswijk, Netherlands; dated Jan. 20, 2016.
(Continued)

*Primary Examiner* — Taeho Jo
(74) *Attorney, Agent, or Firm* — Thomas E. Lees, LLC

(57) ABSTRACT

Detecting threat materials used in explosives is performed by receiving a sample, and selecting an area of interest on the sample suspected of containing a threat material indicative of an explosive. Detection also includes interrogating the area of interest with a Raman laser producing a Raman spectrum, and comparing an amplitude of a first spectral region in the Raman spectrum to a first predetermined threshold. Detection further includes performing a verification, if the determination indicates that the area of interest includes the threat material, by checking the interrogated area of interest for a secondary indicator of the presence of the threat material, by comparing an amplitude of a second spectral region in the Raman spectrum, which is different from the first spectral region in the Raman spectrum, to a second predetermined threshold, and activating an indicator if the verification indicates that the area of interest contains the threat material.

18 Claims, 4 Drawing Sheets

Related U.S. Application Data continuation of application No. PCT/US2015/026302, filed on Apr. 17, 2015.

(60) Provisional application No. 61/980,636, filed on Apr. 17, 2014.

(51) Int. Cl.
*G01N 33/22* (2006.01)
*G01N 21/35* (2014.01)
*G01N 33/00* (2006.01)

(52) U.S. Cl.
CPC . *G01N 33/0057* (2013.01); *G01N 2021/3595* (2013.01)

(58) Field of Classification Search
CPC .... G01N 21/35; G01N 21/6402; G01N 21/94; G01N 21/64; G01N 2201/101; G01N 2001/024; G01N 2021/6421; G01N 33/22; G01N 33/0057; G01N 2021/3595
USPC .................................................. 250/339.07
See application file for complete search history.

(56) References Cited

U.S. PATENT DOCUMENTS

| | | | |
|---|---|---|---|
| 6,882,419 B2 | 4/2005 | Coleman et al. | |
| 7,151,447 B1 | 12/2006 | Willms et al. | |
| 7,420,664 B2 | 9/2008 | Treado et al. | |
| 7,499,167 B2 | 3/2009 | Laudo | |
| 7,543,478 B2 | 6/2009 | Burroughs et al. | |
| 7,606,274 B2 | 10/2009 | Mirov et al. | |
| 7,692,775 B2 | 4/2010 | Treado et al. | |
| 7,692,776 B2 | 4/2010 | Treado et al. | |
| 7,899,650 B2 | 3/2011 | Yeshwantpur et al. | |
| 7,933,013 B2 | 4/2011 | Li | |
| 7,955,855 B2 | 6/2011 | Rothschild et al. | |
| 7,993,585 B2 | 8/2011 | Black et al. | |
| 8,264,681 B2 * | 9/2012 | Misra | G01J 3/02 356/300 |
| 8,363,215 B2 * | 1/2013 | Henry | G01J 3/02 356/300 |
| 8,582,089 B2 * | 11/2013 | Nelson | G01J 3/02 356/73 |
| 8,994,934 B1 * | 3/2015 | Nelson | G01N 33/0057 356/73 |
| 9,097,676 B2 * | 8/2015 | Meinhart | G01N 21/05 |
| 9,335,267 B2 * | 5/2016 | Sausa | G01N 21/3563 |
| 9,395,311 B2 * | 7/2016 | Butler | G01N 21/35 |
| 2004/0051867 A1 * | 3/2004 | Brestel | G01J 3/2889 356/318 |
| 2005/0105099 A1 * | 5/2005 | Shpantzer | G01N 21/171 356/517 |
| 2005/0280827 A1 | 12/2005 | Potma et al. | |
| 2006/0077377 A1 * | 4/2006 | Brestel | G07C 9/00087 356/72 |
| 2007/0056388 A1 | 3/2007 | Henry et al. | |
| 2007/0085998 A1 * | 4/2007 | Brestel | G01J 3/2889 356/73 |
| 2008/0223109 A1 | 9/2008 | Nitta et al. | |
| 2009/0012723 A1 | 1/2009 | Treado et al. | |
| 2009/0027674 A1 * | 1/2009 | Laudo | G01N 15/0255 356/417 |
| 2009/0066946 A1 * | 3/2009 | Wang | G01N 21/648 356/301 |
| 2009/0128802 A1 | 5/2009 | Treado et al. | |
| 2009/0290142 A1 | 11/2009 | Li | |
| 2009/0303471 A1 | 12/2009 | Treado et al. | |
| 2010/0044570 A1 | 2/2010 | McGill et al. | |
| 2010/0085564 A1 * | 4/2010 | Guo | G01J 3/02 356/301 |
| 2010/0171951 A1 * | 7/2010 | Misra | G01J 3/02 356/301 |
| 2010/0225899 A1 | 9/2010 | Treado et al. | |
| 2010/0246610 A1 | 9/2010 | Mirov et al. | |
| 2010/0309464 A1 * | 12/2010 | Treado | G01J 3/0218 356/301 |
| 2011/0080577 A1 * | 4/2011 | Nelson | G01J 3/02 356/73 |
| 2011/0089323 A1 | 4/2011 | Treado et al. | |
| 2011/0112772 A1 | 5/2011 | Yost et al. | |
| 2011/0233428 A1 | 9/2011 | Rothschild et al. | |
| 2011/0242533 A1 | 10/2011 | Treado et al. | |
| 2011/0261351 A1 * | 10/2011 | Treado | G01J 3/32 356/73 |
| 2011/0299071 A1 * | 12/2011 | Treado | G01N 21/64 356/301 |
| 2012/0038908 A1 * | 2/2012 | Beckstead | G01J 3/02 356/72 |
| 2012/0044478 A1 | 2/2012 | Da Re et al. | |
| 2012/0062740 A1 * | 3/2012 | Treado | G01J 3/0264 348/144 |
| 2012/0062874 A1 * | 3/2012 | Beckstead | G01J 3/02 356/72 |
| 2012/0133932 A1 * | 5/2012 | Henry | G01J 3/02 356/301 |
| 2012/0134582 A1 * | 5/2012 | Treado | G01J 3/28 382/165 |
| 2012/0147358 A1 * | 6/2012 | Gardner, Jr. | G01J 3/02 356/72 |
| 2012/0198912 A1 * | 8/2012 | Ewing | G01N 1/22 73/23.35 |
| 2013/0341509 A1 * | 12/2013 | Nelson | G01J 3/0248 250/330 |
| 2014/0043488 A1 * | 2/2014 | Treado | G01J 3/0278 348/164 |
| 2014/0060189 A1 * | 3/2014 | Sausa | G01N 21/3563 73/579 |
| 2014/0233035 A1 * | 8/2014 | Islam | H01S 5/0064 356/456 |
| 2015/0004684 A1 * | 1/2015 | Meinhart | G01N 21/05 435/288.7 |
| 2015/0069258 A1 * | 3/2015 | Butler | G01N 21/35 250/395 |
| 2015/0192462 A1 * | 7/2015 | Schiering | G01J 3/44 250/208.2 |
| 2016/0069810 A1 * | 3/2016 | Walavalkar | G01N 21/658 356/301 |
| 2016/0178525 A1 * | 6/2016 | Umapathy | G01N 21/65 356/301 |

OTHER PUBLICATIONS

Willer, U. et al.; "Photonic Sensor Devices for Explosive Detection"; Analytical and Bioanalytical Chemistry; Springer; Berlin, Germany; vol. 395; Jul. 14, 2009.

Ali, E. M.A. et al.; "In-situ Detection of Single Particles of Explosive on Clothing with Confocal Raman Microscopy"; Talanta; Elsevier; Amsterdam, Netherlands; vol. 78; 2009.

Notification Concerning Transmittal of International Preliminary Report on Patentability and Written Opinion of the International Searching Authority for International PCT Application No. PCT/US2015/026302; The International Bureau of WIPO; Geneva, Switzerland; dated Oct. 27, 2016.

Weinberger, Thorsten; European Office Action for European Application No. 15784501.7; European Patent Office; Munich, Germany; dated May 22, 2018.

Japanese Office Action for Japanese Patent Application No. 2016-562968; Japanese Patent Office; dated Apr. 23, 2019.

Ken Fujisawa et al.; "Comparison of Each Qualitative Analytical Outputs Obtained of Infrared Spectroscopy, Raman Spectroscopy and Scanning Electron Microscope/Energy Dispersion X-ray Spectrometer (SEM-EDS) of Some Compounds", No. 6, P.M6-M9; 2011.

(56) References Cited

OTHER PUBLICATIONS

Jimmie C. Oxley et al.; "Synthesis and Characterization of Urea Nitrate and Nitrourea"; Propellants, Explosives, Pyrotechnics; vol. 38/Iss. 3; pp. 1-25; Apr. 15, 2013.

* cited by examiner

EXPLOSIVES DETECTION USING OPTICAL SPECTROSCOPY

CROSS REFERENCE TO RELATED APPLICATIONS

This application is a continuation of U.S. patent application Ser. No. 15/292,253, filed Oct. 13, 2016, entitled "Explosive Detection Using Optical Spectroscopy", now allowed, which is a bypass continuation of International Application No. PCT/US2015/026302, filed Apr. 17, 2015, entitled "EXPLOSIVES DETECTION USING OPTICAL SPECTROSCOPY", which claims the benefit of U.S. Provisional Patent Application Ser. No. 61/980,636, filed Apr. 17, 2014, entitled "EXPLOSIVES DETECTION USING OPTICAL SPECTROSCOPY", the disclosures of which are hereby incorporated by reference.

BACKGROUND

Various aspects of the present invention relate generally to explosives detection and specifically to the use of optical spectroscopy to detect explosives.

An improvised explosive device (IED) is a typically implemented as a homemade bomb, which can be constructed and deployed differently than conventional military means. For instance, in some cases, IEDs are constructed from conventional, everyday objects including ammonium nitrate fertilizers, steel pipes, pressure cookers, etc.

BRIEF SUMMARY

According to aspects of the present disclosure herein, a method for detecting threat materials used in explosives is provided. The method comprises receiving a sample, and selecting an area of interest on the sample suspected of containing a threat material. The method also comprises interrogating the area of interest, with a Raman laser, thereby producing a Raman spectrum, and determining whether the area of interest includes the threat material by comparing an amplitude of a first spectral region in the Raman spectrum, to a first predetermined threshold. The method still further comprises performing a verification, if the determination indicates that the area of interest includes the threat material, by checking the interrogated area of interest for a secondary indicator of the presence of the threat material, where the verification is performed by comparing an amplitude of a second spectral region in the Raman spectrum, which is different from the first spectral region in the Raman spectrum, to a second predetermined threshold. Moreover, the method comprises activating an indicator if the verification indicates that the area of interest contains the threat material.

According to further aspects of the present disclosure, the method only performs the verification if the determination indicates that the area of interest includes the threat material, e.g., if the amplitude of the first spectral region is greater than the first predetermined threshold.

Moreover, the method may comprise selecting the first spectral region, the second spectral region, or both, as a region that is sufficiently small to capture a single feature distinguishable from the measured spectrum. For instance, where the threat material is a nitrate, the method performs interrogation of the area of interest with the Raman laser to produce the Raman spectrum, wherein the Raman spectrum is measured in the first spectral region, which is set to a wave number shift around 1050 cm$^{-1}$. In this manner, the method compares the amplitude of the measured portion of the Raman spectrum at approximately 1050 cm$^{-1}$ to the predetermined threshold, where the predetermined threshold is set to a value indicative of a nitrate, as a nitrate is expected to have a distinguishing feature in this area. Moreover, the method performs the verification by checking for a feature at the second spectral range (e.g., which is set to a wave number shift around 3225 cm$^{-1}$ to detect ammonium nitrate as ammonium nitrate is expected to have a distinguishing feature in this area). As another example, the method may perform the verification by checking for a feature at a wave number shift around 550 cm$^{-1}$ for urea nitrate as urea nitrate is expected to have a distinguishing feature in this area.

According to further aspects of the present invention, a system for detecting threat materials used in explosives, comprises a sample collector, a sample stage, an interrogation station that includes a Raman laser source, a processor coupled to memory, and an output device. The sample collector collects a sample, and the sample stage receives the sample from the sample collector. The processor is further programmed to interact with the interrogation station to interrogate, with the Raman laser source, the area of interest thereby producing a Raman spectrum, and to determine whether the area of interest includes the threat material by comparing an amplitude of a first spectral region in the Raman spectrum, to a first predetermined threshold. The processor is further programmed to perform a verification, if the determination indicates that the area of interest includes the threat material, by checking the interrogated area of interest for a secondary indicator of the presence of the threat material, where the verification is performed by comparing an amplitude of a second spectral region in the Raman spectrum, which is different from the first spectral region in the Raman spectrum, to a second predetermined threshold. Moreover, the processor is programmed to activate an indicator if the verification indicates that the sample contains the threat material.

DETAILED DESCRIPTION

Various aspects of the present disclosure provide systems and methods for detecting, characterizing, or both detecting and characterizing, threat materials such as explosives using optical spectroscopy. Some of the systems are portable to bring on-site to detect explosives before the explosives have a chance to vaporize. Further, the systems and methods can detect the explosive in particulate form, which reduces reliance on dissolved or reacted materials that may give a false positives with common environmental salts that also include explosive base materials (e.g., ammonium nitrates, urea nitrates, etc.). The explosive may be detected from an unexploded state or a post-blast (i.e., exploded) state. Further analysis can be performed on the explosive to determine the source of the explosive, including the process and materials used to make the explosive. In this regard, systems and methods are provided, which are capable of detecting explosives, including homemade explosives, without the requirement to perturb the native state of the explosives.

Figure 1:
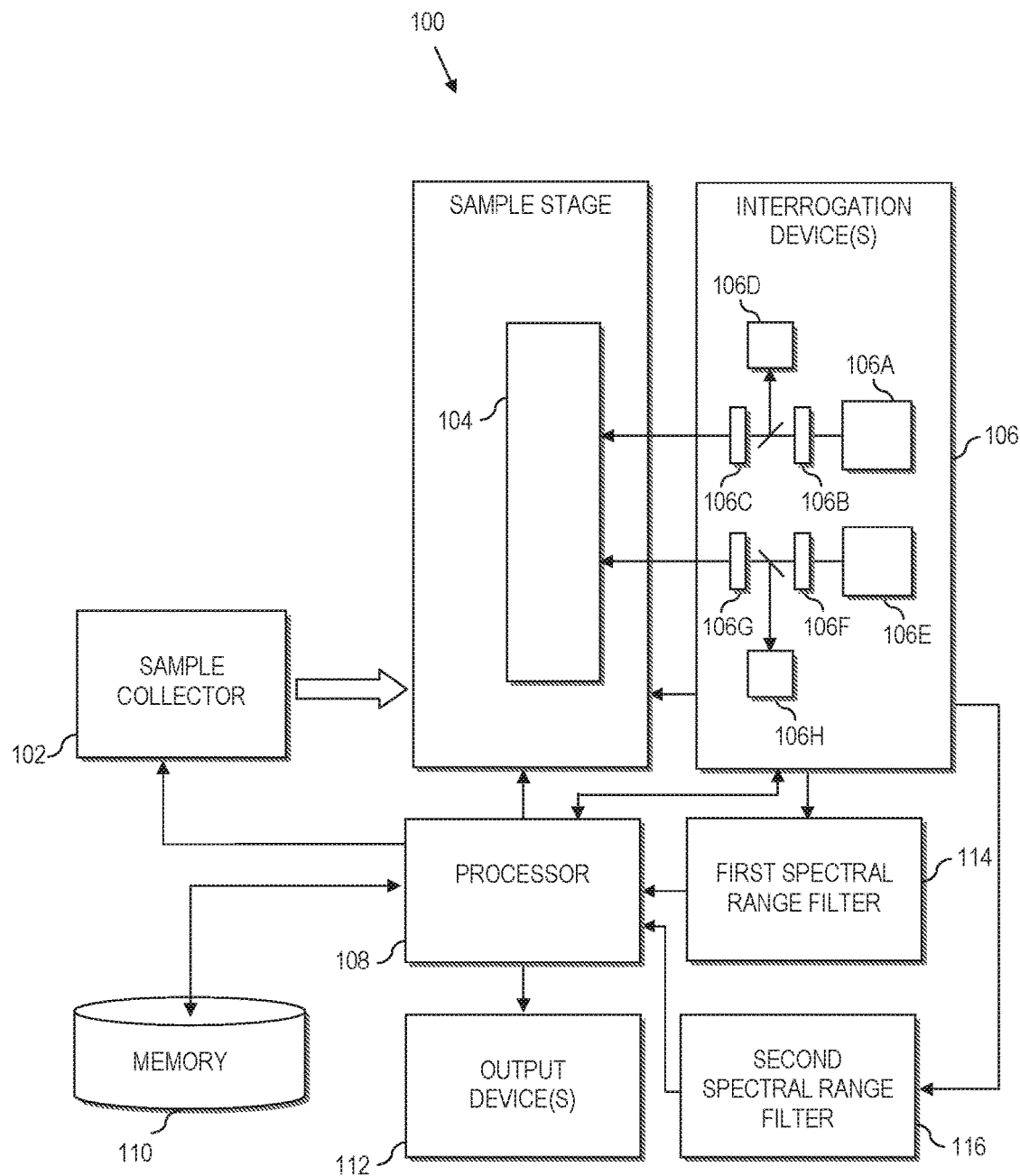
FIG. 1 is a block diagram of an illustrative system detecting explosives using optical spectroscopy, according to various aspects of the present disclosure.

System Overview:

Referring now to the drawings, and in particular to FIG. 1, a system 100 for detecting explosives using optical spectroscopy is illustrated, according to various aspects of the present disclosure. The system 100 includes in general, a sample collector 102 that provides a sample that may contain a threat material, such as may be found in explosives. The sample collected by the sample collector 102 is positioned for analysis on a sample stage 104 for interrogation by one or more interrogation devices of an interrogation station 106. Interrogation devices include for instance, a Raman spectrometer fluorescence system, imaging camera and microscope, combinations thereof, etc. In some embodiments, a processor 108 is used to control the sample collector 102, the sample stage 104, one or more of the interrogation device(s) of the interrogation station 106, combinations of the above, etc.

Further, the processor 108 can access an output device 112 such as an indicator used to sound an alarm, to report out the results of a sample analysis, etc. The output device 112 can also include a screen, printout, transmission device (cellular, network, etc.) or other suitable device, to convey information, including measurements, analysis results, an analysis of a detected explosive, an indication of the source of the explosive, or combination thereof. A determination of the source of the explosive can include the process used to make the detected explosive and/or materials used to make the explosive.

In this regard, the processor 108 interacts with memory 110 to store threshold variables, control instructions, set points, interrogation control parameters, evaluation algorithms, any other necessary information to perform explosives detection, etc., as set out herein. Moreover, the memory 110 can be used by the processor 108 to store measurements, evaluation data, evaluation results, or other information that is generated during use. Further, by coupling the processor 110 to the memory 110, the processor 108 is programmed to interact with the sample collector 102, sample stage 104, interrogation station 106, output device(s) 112, or combinations thereof, to implement the functions set out in greater detail herein, including the method 200 of FIG. 2, discussed herein.

In use, a sample is received (e.g., from the sample collector 102, which may be integral to the remainder of the system 100, or implemented as a separate component). In an illustrative example, the sample is received onto the sample stage 104, such as a multi-axis motorized stage that is controlled by the processor 108 to move the sample relative to the stage in the X dimension, Y dimension, Z dimension, or combination thereof, to evaluate the collected sample. For instance, depending upon the collected sample, the sample area may be as large as 2 millimeters×2 millimeters. However, a particulate that is a threat material may be approximately 1-2 microns or less. As such, the sample stage 104 may be a motorized stage having a high degree of accuracy (e.g., to a resolution of 0.1 microns).

According to an illustrative example of the present disclosure, interrogation device(s) may be implemented within, or otherwise coordinated with the optical interrogation station 106. In some embodiments, a first interrogation device is implemented as a first optical device that includes a first illumination source 106A (e.g., a Xenon arc source), which directs a first light beam through any appropriate lenses, filters, or other optical devices 106B, and through an optional element 106C such as an objective lens, towards the sample. In this regard, the sample has been advanced to a sample substrate receiving area 104A of the sample stage 104. Light from the surface of sample is reflected and is focused onto a camera 106D to form an image of the sample. This image comprises first data that is processed by the processor 108, and which may be used to determine one or more target locations and/or fields of view, which may be of interest for further interrogation. Here, the target locations (i.e., areas of interest) are detected by the processor 108 (e.g., using techniques such as detecting fluorescence, bright field image processing or dark field image processing, as will be described in greater detail herein).

The processor 108 thus selects a target location (area of interest on the sample), which is suspected of containing a threat material, and interrogates that targeted location. For instance, in some embodiments, a second interrogation device is implemented as a second optical device 106E that provides a beam from a suitable laser source, which passes through any appropriate lenses, filters, or other optical devices 104F, and is optionally focused by an element 106G, e.g., an objective lens, onto the sample. For instance, the beam from the second optical device 106E is directed at the specific areas of interest that are specified from the target locations identified by the processor 108, e.g., based upon an analysis of the first data. The second beam is reflected from the sample, where the second beam is directed to a spectrometer 106H, such as a Raman spectrometer. The interrogation data from the second optical device 106E (e.g., a targeted vibrational analysis produced by Raman spectroscopy that is recorded by the spectrometer 106H) is used to identify whether the targeted area of interest includes a threat material such as an ingredient of an explosive, such as a nitrate, as will be described in greater detail herein.

The specific components described above with reference to the interrogation station 106 are discussed and schematically illustrated as separate components for clarity of discussion. However, in practice, components that make up the interrogation device(s) may be independent or shared. Likewise, there may be a single interrogation device or multiple interrogation devices, so long as the described functions (e.g., targeting and targeted interrogation) are capable of being performed.

The processor 108 determines whether the area of interest includes the threat material by comparing an amplitude of a first spectral region measured during the interrogation, to a first predetermined threshold. In FIG. 1, the first spectral region is illustrated in block diagram form, as being extracted by a first spectral range filter 114. The first spectral range filter can be an optical filter (e.g., a narrow bandpass filter) or the first spectral range filter 114 can be implemented digitally by the processor 108. The first threshold is extracted from the memory 110 for the comparison. If (and only if) the determination indicates that the area of interest includes the threat material, the system performs a verification. The verification is performed by comparing an amplitude of a second spectral region different from the first spectral region, measured during the interrogation, to a second predetermined threshold. In FIG. 1, the second spectral region is illustrated in block diagram form, as being extracted by a second spectral range filter 116. The second spectral range filter can be an optical filter (e.g., a narrow bandpass filter) or the second spectral range filter 116 can be implemented digitally by the processor 108.

The processor 108 activates the output device 112 if the verification indicates that the sample contains the threat material. In this regard, the processor 108 interacts with the indicator 112 to communicate the results of the analysis to a user. Moreover, the processor 108 discriminates between specific threat material(s) of interest (determined by detection and verification) and other particulates that have been collected.

Figure 2:
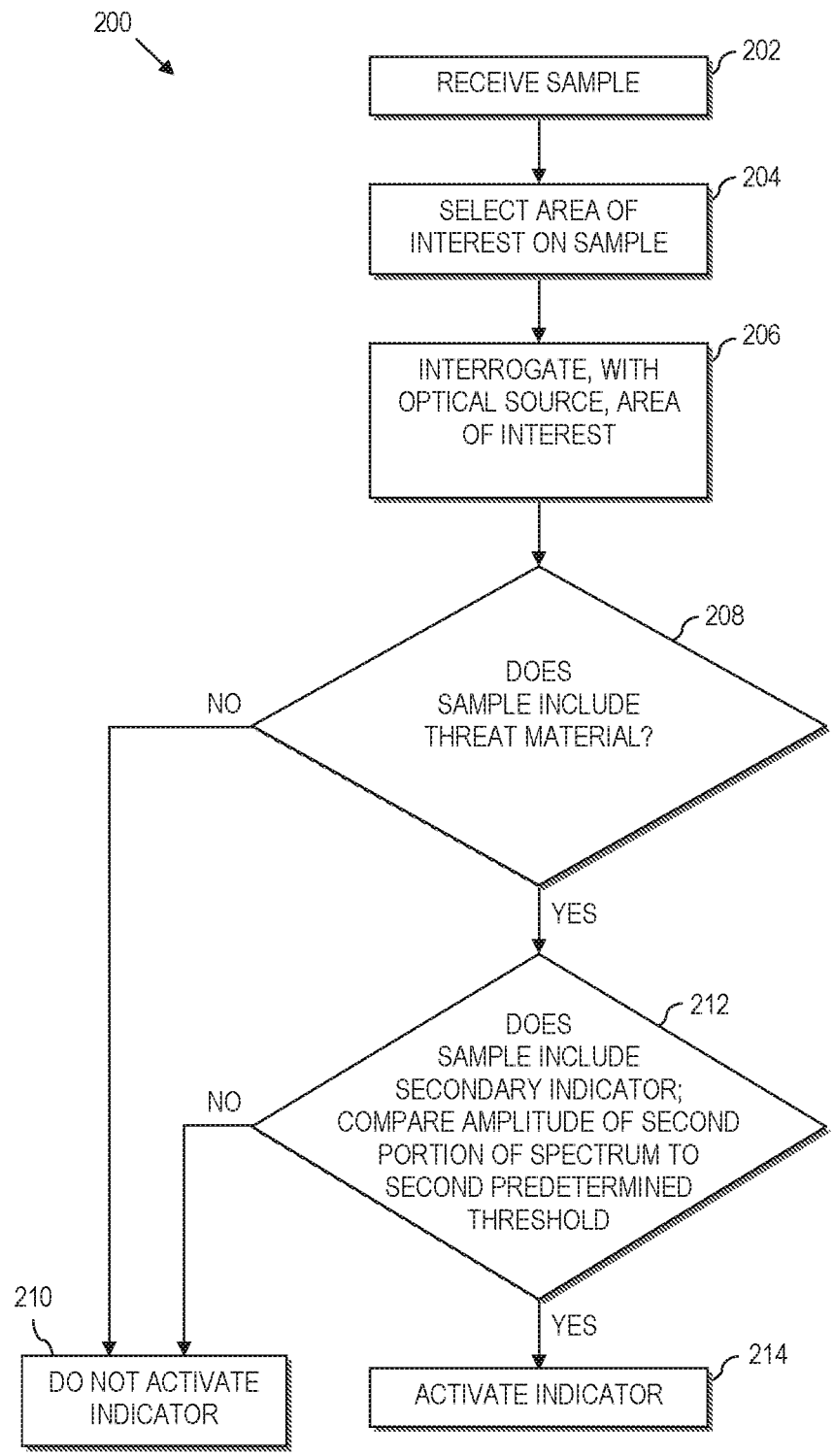
FIG. 2 is a flow chart illustrating a method for detecting explosives using optical spectroscopy, according to various aspects of the present disclosure.

Method of Detecting a Threat Material:

Referring to FIG. 2, a method 200 for detecting explosives (including explosive precursors and post-blast products) using optical spectroscopy is shown. The method 200 may be implemented, for instance, on the system 100 of FIG. 1.

The method 200 includes receiving at 202, a sample. The sample may be received at 202, in any applicable way.

Collection:

In exemplary implementations, the sample collector 102 of FIG. 1 can be used to collect a sample, which is received by the method 200. For instance, a sample collector can be implemented as a collection system that is configured to collect a sample onto a sample substrate (e.g., a non-Raman active membrane filter material or other form of filter material). The collection device may comprise, for example, a collector, solid surface small area impactor, electrostatic precipitation device, cyclone device, or other collection technology.

In an illustrative example, the collection device draws and accelerates a fluid stream, such as from the ambient air, through the collector. Particulate matter that is entrained in the stream is extracted and deposited onto a sample substrate (e.g., the filter) in a relatively small, defined sample area. The filter may be manually placed in the collection system or the filter may be automatically placed in the collection system (e.g., via a translation subsystem).

Examples of a suitable collection device to create the sample are disclosed in U.S. Pat. No. 7,499,167, entitled "AEROSOL TRIGGER DEVICE AND METHODS OF DETECTING PARTICULATES OF INTEREST USING AN AEROSOL TRIGGER DEVICE" filed Jul. 14, 2006 by Rodney S. Black et al., and in U.S. Pat. No. 7,993,585 entitled "BIOLOGICAL AND CHEMICAL MONITORING" filed on Jul. 14, 2006 by Rodney S. Black et al., the disclosures of which are hereby incorporated by reference in their entirety.

For instance, the collection device may include a pre-impactor to filter particulates in the fluid stream to a generally predetermined size. As further examples, the collector may be implemented by a device that exhibits high efficiency, low pressure differential particulate collection, aerodynamic particle size filtration, and which can provide uniform coverage of a planar and flat surface with particulate matter. Thus, the collection system can provide homogeneous spatial distribution of particulate matter onto a sample substrate.

As mentioned above, the sample may be created by impacting a fluid stream onto a substrate. Any type of substrate may be used including an aluminum substrate. However, it has been found through experimentation that a gold substrate (plated or solid) may be preferred, because the gold substrate preserves the sample longer than an aluminum substrate, especially when the sample includes ammonium nitrate. For instance, the ammonium nitrate may chemically react with the aluminum, leading to a more rapid loss of the sample than on a gold substrate.

Another example of receiving a sample is to receive a sample that was previously collected, placed, or otherwise presented on a substrate.

The sample may be enclosed in a relatively small container to prevent evaporative loss of small particles of explosive. For example, the sample may include ammonium nitrate. However, when ammonium nitrate dissociates, the result is ammonia and nitric acid; both of which are volatile. If these ammonia and nitric acid molecules are lost to the atmosphere, the rate of sample loss to evaporation is higher than would be expected from just the vapor pressure of ammonium nitrate. Because the ammonia and nitric acid molecules are continually lost, no equilibrium is established and the ammonium nitrate continually dissociates. Thus, to preserve the sample, it may be desirable to contain the sample inside a relatively small, enclosed container.

On the other hand, the sample may be in an open environment or otherwise not contained in an enclosed container after impacting the substrate. For instance, the sample may be received onto a sample substrate in an open environment, e.g., through impaction by a collector described herein, which can be implemented as part of an integral or otherwise automated optical system, e.g., as described with reference to FIG. 1. Such a system allows the sample to be processed on-site or relatively quickly after collection.

Evaluation:

The method 200 also comprises selecting, at 204, an area of interest on the sample, which is suspected of containing a threat material. For example, the sample may be affected with a fluorescent marker or a contrast dye. A fluorescent optical device (e.g., deep ultraviolet excitation device) may illuminate the sample, and the areas that fluoresce may be selected as areas of interest. As yet an additional example, a first optical device can use spectral "fingerprints" to classify, identify and/or distinguish sample regions or specific particulates within sample regions for additional targeted interrogation. Selective spectral regions may contain strong scattering features that are indicative of a class of particles. In this way spectral regions can be used in a manner similar to fluorescence emission as a discrimination tool. As another example, the location of particulates formed in the sample may be affected by the particulate size, e.g., particulate size may decrease with the distance within the sample from the center of the nozzle of the collector. This information may be utilized, for example, when selecting target locations based, at least in part, upon particulates of a predetermined size range.

Moreover, darkfield, lightfield, and other optical processing techniques can be used to identify particulates that may be of interest. On the other hand, the area of interest may be selected with a raster scan of the sample, where the entire sample is eventually interrogated. The selected area for targeted evaluation may be down to a single particle size. In this regard, various techniques above can be combined in any desired combination. For instance, a bright field image can be compared to a fluorescence image, etc. Another exemplary technique comprises the use of images, e.g., from a camera for the selection of specific sizes and/or shapes of target particulates. Targeting a particular size range by image processing may thus increase the likelihood of identifying particulates that may be of interest. Using corresponding image processing techniques, particles of a specific size range and/or shape can be located in the field of view for interrogation. Still further, discrimination techniques can be used to "rule out" areas as being of interest.

As such, the presence of various matrix (sand, dust, lint) and interferent materials does not affect the detection accuracy. The selection of the area (or areas) of interest may be carried out, for instance, by one or more of the interrogation device(s) of the interrogation station 106 and the processor 108 of FIG. 1.

The process at 204 may thus be utilized to segregate innocuous materials from targeted materials. Notably, a sample collection area may be on the order of 1 millimeters (mm) to 2 mm squared. However, a particle of interest may be on the order of 1 micron or smaller. As such, the segregation of innocuous material significantly speeds up the evaluation process.

The method 200 also comprises interrogating, at 206, with an optical source, the area of interest. For example, a Raman laser may be used to interrogate the area of interest to produce a Raman spectrum of a portion of the area of interest. Another example is using interferometric spectroscopy to interrogate at least a portion of the area of interest to produce a spectrum of the portion of the area of interest. For instance, the interrogation at 206 may be carried out by a laser and Raman spectrometer of the interrogation station 106, and the processor 108 of FIG. 1.

The method 200 also includes determining, at 208, whether the area of interest includes the threat material by comparing an amplitude of a first spectral region measured during the interrogation, to a first predetermined threshold. For instance, a first portion of a spectrum (or series of spectra) is compared to a first predetermined threshold to determine if the sample includes a component of a threat material (e.g., an explosive including a nitrate). The determination may be performed, for instance, by the interrogation station 106, processor 108, memory 110, and first spectral range filter 114 of FIG. 1.

By way of example, when using Raman spectroscopy, the amplitude of the spectrum at approximately 1050 $cm^{-1}$ will be greater than the surrounding spectrum values if a nitrate is present. That is, the spectrum exhibits a spike at around 1050 $cm^{-1}$. Therefore, if the amplitude of the spectrum at 1050 $cm^{-1}$ of the Raman spectrum is above a certain level (the predetermined first threshold level), then the sample may be said to include a nitrate. Thus, in an example implementation, the method 200 comprises interrogating at least a portion of the area of interest with a Raman laser to produce a Raman spectrum, wherein the Raman spectrum is measured in the first spectral region, which is set to a wave number shift around 1050 $cm^{-1}$. As such, the method 200 may also comprise comparing the amplitude of the measured portion of the Raman spectrum at approximately 1050 $cm^{-1}$ to the predetermined threshold, where the predetermined threshold is set to a value corresponding to a feature in the first spectral range that is indicative of a nitrate.

Notably, here, the first spectral region can be selected as a narrow region, e.g., a region that is sufficiently small to capture a single feature of the captured spectrum, such as the spike around 1050 $cm^{-1}$ that is indicative of a nitrate. In practice, other threat materials will likely have a defining feature in a different wavenumber shift. As such, the first spectral range is selected as a range large enough to capture the feature or features in the Raman spectrum that are of interest. However, the tighter the filter (i.e., the smaller the spectral range), the less computationally intensive, and hence, the faster the initial evaluation is. For instance, in an example implementation, the method uses a first spectral range filter, e.g., a fixed narrow bandpass filter that filters the spectrum from the sample to an isolated, narrow spectral range, e.g., potentially as narrow as to a specific wave number shift, such as around 1050 $cm^{-1}$. Correspondingly, the method at 206, evaluates spectral information solely within the narrow spectral range, e.g., by the processor 108 of FIG. 1. This approach minimizes the amount of data that must be analyzed. Also, this approach eliminates the complexity of an adjustable or otherwise tunable filter. Moreover, this approach eliminates the processing delays inherent in controlling a tunable or otherwise adjustable filter, which may take too long to adjust given the volatility of the sample to vaporize or dissociate, especially when evaluating a post-blast environment.

If no nitrate is found, the method 200 may loop to 204 to select another area of interest on the sample or the method 200 may end. If the method 200 ends without detecting a threat material at all, then the method 200 may end at 210 without activating an indicator that indicates that an explosive is found.

However, if a threat material (e.g., a nitrate) is found (i.e., if the determination indicates that the area of interest includes the threat material), then the method 200 performs a verification. Thus, the method 200 may only perform the verification if the amplitude of the first spectral region is greater than the first predetermined threshold.

More particularly, the method 200 comprises performing, at 212, a verification by checking for a secondary indicator of the presence of the threat material, where the verification is performed by comparing an amplitude of a second spectral region different from the first spectral region, measured during the interrogation, to a second predetermined threshold. The verification may be performed, for instance, by the interrogation station 106, processor 108, memory 110, and second spectral range filter 116 of FIG. 1.

In an example implementation, at 212, a second portion of a spectrum (or series of spectra) is compared to a second predetermined threshold to determine if the sample includes a secondary indicator of an explosive. In other words, once the method 200 has determined the presence of a threat material (e.g., a nitrate) in the sample, the method 200 looks for other secondary indicators of an explosive (e.g., ammonia for ammonium nitrate, urea for urea nitrate, etc.).

For example, when using Raman spectroscopy, the amplitude of the spectrum at approximately 3225 $cm^{-1}$ will be greater if ammonia is present or approximately 550 $cm^{-1}$ will be greater if urea is present.

More particularly, the method 200 may perform the verification by interrogating at least a portion of the area of interest with a Raman laser to produce a Raman spectrum, wherein the Raman spectrum is measured in the second spectral region, which is set to a wave number shift around 3225 $cm^{-1}$, and determining if the sample includes ammonium nitrate by comparing the amplitude of the measured portion of the Raman spectrum at approximately 3225 $cm^{-1}$ to the predetermined threshold, where the second threshold is set to a value corresponding to a feature in the second spectral range indicative of ammonium nitrate.

Similarly, the method 200 may perform the verification by interrogating at least a portion of the area of interest with a Raman laser to produce a Raman spectrum, wherein the Raman spectrum is measured in the second spectral region, which is set to a wave number shift around 550 $cm^{-1}$ and determining if the sample includes urea nitrate by comparing the amplitude of the measured portion of the Raman spectrum at approximately 550 $cm^{-1}$ to the predetermined threshold, where the second threshold is set to a value corresponding to a feature in the second spectral range indicative of urea nitrate.

If no secondary indicator of an explosive is present, then the method 200 may loop back to select a new area of interest or end. However, if a secondary indicator is detected, then at 214, an indicator is activated to signal that an explosive is present in the sample. The indicator may be any appropriate signal such as a light, a buzzer, a printout, a display (e.g., a monitor, LED display, LCD display, etc.), an e-mail, a text message, etc.

The method may ultimately continue with additional analysis, such as storing information while the collection system continues to collect samples that are analyzed to develop trends. Moreover, once a material is determined to be a threat material, more detailed analysis can be carried out. For instance, signatures can be utilized to identify the material with specificity. Samples can be continuously collected to estimate concentration, etc. For instance, the processor 108 can compare the collected spectra (e.g., a more complete version of the spectrum than used at 208 and 212) to signatures stored in the memory 110 to identify the specific nature of the threat material. The signatures can also be used to provide insight into identifying the process and materials used to make the explosive, such as by combining the results of the signature analysis with domain knowledge programmed into the memory 110 of FIG. 1.

Spectroscopy

To perform the interrogation at 206, a spectrometer may be used. In illustrative examples, a high throughput spectrometer may be utilized to evaluate the sample (e.g., using $10^6$ off-axis diffuse light rejection, optimized Etendue for scattering collection optics, etc.). The system should be capable of spatial and spectral separation. However, spatial separation may not be necessary, such as if laser scanning is used. In illustrative implementations, the spectrometer is polarization dispersion invariant, and capable of broad spectral coverage and high spectral resolution to improve target identification.

Moreover, the system may utilize an interferometric method that reduces system requirements by removing the grating dispersion element (e.g., removing the need of a 2-D detector). However, a thermoelectric-cooled linear array of finite elements may be utilized as the detector.

Further, the spectrometer may utilize a high collection angle, narrow depth-of-field system, coupled with fully automated image collection and processing, followed by automated targeting of selected particles (e.g., starting at 204 of the method 200), thus facilitating the ability to quickly analyze particles as small as 300 nm diameter.

Observations:

The method 200 implements a two-determination process in evaluating a spectrum to determine a presence of an explosive in a sample. In the first determination (e.g., 208), the spectrum is checked only around a certain range to determine a presence of an indicator of an explosive (e.g., a feature in the spectrum that is indicative of a nitrate). For example, in a Raman spectrum collected from the sample, a narrow range around 1050 $cm^{-1}$ may be checked for the presence of a nitrate. All other portions of the spectrum may be ignored during this first determination. If (and thus only after) a nitrate is found, the second determination checks for a secondary indicator of an explosive. Again, the spectrum is checked only around the ranges of the secondary indicators (e.g., ~3225 $cm^{-1}$ for a feature indicative of ammonia, ~550 $cm^{-1}$ for a feature indicative of urea, etc.). For example, to determine if a sample includes ammonium nitrate using Raman spectroscopy, the Raman spectrum of the sample need only be compared at approximately 1050 $cm^{-1}$ and 3225 $cm^{-1}$.

Further, more than one spectrum may be created. For example, the spectrum used in the first determination may be created using a Raman laser, and the spectrum used in the second determination may be created using interferometric spectroscopy. As another example, the spectrum used in the first determination may be created using a Raman laser of a first wavelength, and the spectrum used in the second determination may be created using a Raman laser of a second wavelength. Different excitation lasers on the same sample may produce different spectra to aid in determining if a sample includes an explosive.

Thus, the explosive detection process according to the method 200 as set out herein, provides faster computation times for processing an entire sample over methods that require the entire sample spectra to be compared to known Raman signatures to determine a presence of an explosive.

Figure 3:
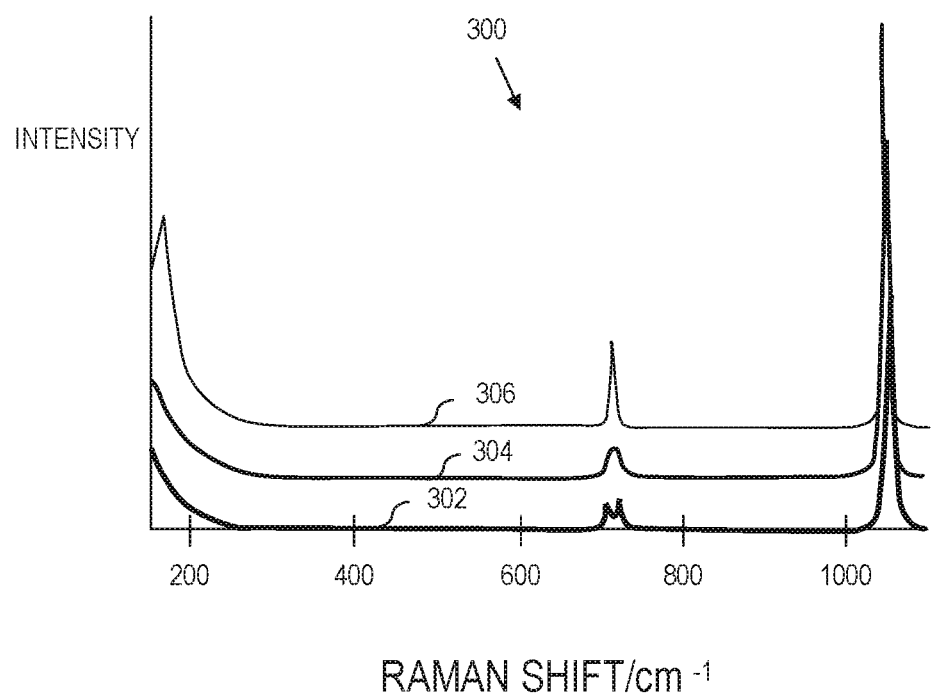
FIG. 3 is a graph illustrating Raman spectra for three phases of ammonium nitrate from 200 to 1100 cm$^{-1}$, according to various aspects of the present disclosure.
Figure 4:
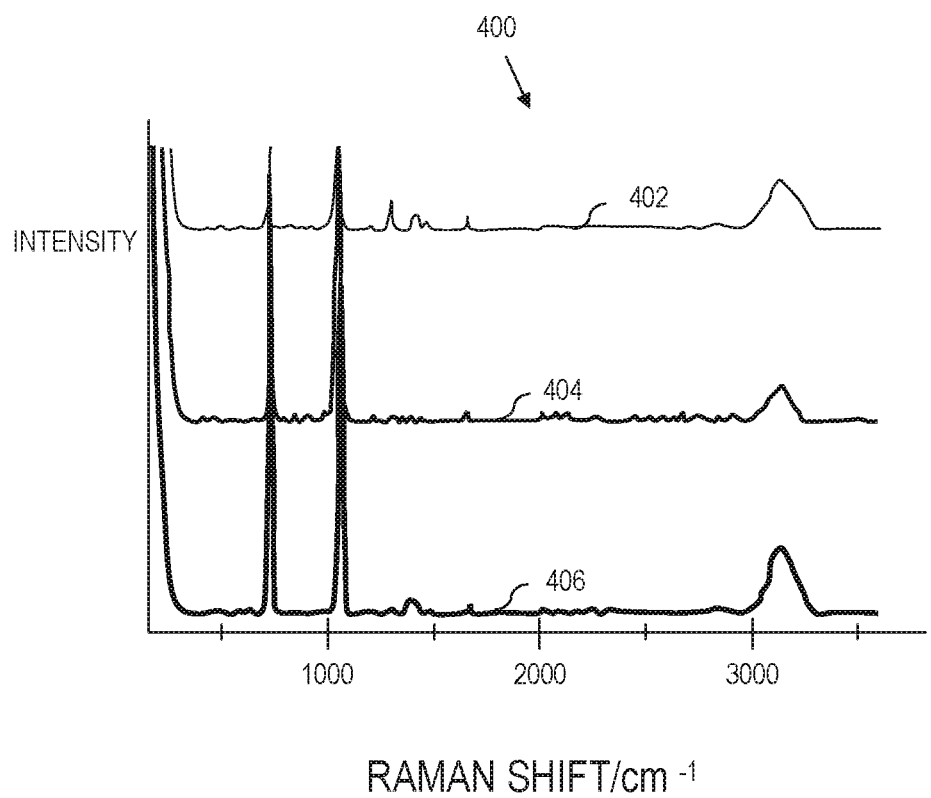
FIG. 4 is a graph illustrating Raman spectra for three phases of ammonium nitrate from 200 to 3500 cm$^{-1}$, according to various aspects of the present disclosure.

Turning now to FIGS. 3-4, Raman spectra of three phases of ammonium nitrate are shown. In FIG. 3, the bottom spectrum 302 shows ammonium nitrate in phase II, the middle spectrum 304 shows ammonium nitrate in phase III, and the top spectrum 306 shows ammonium nitrate in phase IV. Similarly, in FIG. 4, the bottom spectrum 402 shows ammonium nitrate in phase II, the middle spectrum 404 shows ammonium nitrate in phase III, and the top spectrum 406 shows ammonium nitrate in phase IV.

The method 200 of FIG. 2 can use this information to help determine a source of ammonium nitrate found in a sample. For instance, despite the different spectra, each phase of ammonium nitrate exhibits a feature identified by a strong peak at approximately 1050 $cm^{-1}$. As such, a narrow filtered scan in this region can accurately and quickly distinguish each sample as a nitrate.

Crystal Phase Distribution:

Ammonium nitrate exhibits polymorphism and has six stable crystalline phases. Raman spectra distinguish between crystalline phases because the crystalline arrangement determines which vibrations are excited (and therefore observed) and produces shifts in the vibrational energy of some bonds.

Under normal laboratory conditions (approximately 293 K), phase IV is expected to be the dominant phase of ammonium nitrate. However, this is not always the case, because the phase of ammonium nitrate is also dependent on a preparation method. For example, if ammonium nitrate is dissolved and then rapidly dried to generate microscopic crystals, there may be indications of both phases II and III, and these phases can persist for days. Thus, if an explosive is detected in a sample, then the Raman spectra can be compared to the signatures to determine the phase of the explosive, which is indicative of the preparation process of the explosive. That is, field samples may also contain a distribution of crystal phases that is indicative of the ammonium nitrate preparation method, thus providing a forensic tool.

Another method of creating ammonium nitrate can be grinding prills of manufactured calcium ammonium nitrate. Moreover, the storage temperature of the ammonium nitrate may affect the dominant phases of the ammonium nitrate detected in the sample. Therefore, through looking at the phases of the ammonium nitrate in the sample, a storage temperature, manufacturing process, or both may be discovered to help identify the source of the explosive.

Although ammonium nitrate is discussed here, the source of any applicable explosive (including explosive precursors and post-blast products) may be found. For instance, the system 100 of FIG. 1 can be tuned to a desired product or products of interest. As mentioned above, the devices disclosed in U.S. Pat. No. 7,993,585 can be modified to support the system 100 and/or method 200 described herein. As such, in illustrative implementations, explosives, explosive precursors, and post-blast products can be identified using particulate matter down to a picogram in mass or less than 500 nanometers in size.

Sample Persistence:

Conventionally prepared samples of ammonium nitrate may, under some collection and storage conditions, be lost to sublimation, evaporation or chemical reactions within hours or days. However, the system herein can be used to observe particles over time and monitor their loss rates or reaction products. When ammonium nitrate dissociates, it forms ammonia and nitric acid:

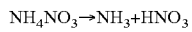

$NH_4NO_3 \rightarrow NH_3 + HNO_3$

Both of these reaction products are volatile. If these molecules are lost to the atmosphere, the rate of sample loss to evaporation is higher than would be expected from the vapor pressure of ammonium nitrate. Because the products are continually lost, no equilibrium is established and the reaction continues to be driven towards the products. In addition to this dissociation and evaporation loss mechanism, it is also possible to lose ammonium nitrate through other chemical reactions. For instance, as noted above, ammonium nitrate placed on an aluminum substrate is lost more rapidly than ammonium nitrate placed on a gold substrate.

Miscellaneous:

Aspects of the present invention herein provide a system that can examine trace quantities of particulate matter down to a picogram in mass/half a micrometer in size. That is, the system described herein is able to identify threat materials based on examining a single, microscopic particle of the target explosive. The evaluation is carried out using microscopy optics, highly sensitive detectors, and pattern recognition software that allows the process from sample collection through identification to be fully automated. As noted in greater detail herein, the system can report the chemical makeup of the sample. Further, as noted in greater detail herein, the system can be programmed to automatically synthesize all of the data and provide information on the likely sample origin. By way of example, there may be forensic information in examining the distribution of the crystalline structure of ammonium nitrate samples. For instance, the crystal structure depends on the material preparation process. As such, examining the crystal structure can reveal information about the source of the ammonium nitrate used in a homemade explosive or other device.

Moreover, Raman signatures as disclosed herein, which allow for the identification of a wide range of chemical compounds, including explosives, their synthesis precursors, and post-blast products.

The system herein has the unique capability of detecting the intact ammonium nitrate and urea nitrate crystals without depending on detecting the dissolved or reacted material. This enables the system to readily distinguish target materials from common environmental salts that also contain ammonium, urea, or nitrate ions.

Conventional methods of explosives detection can dissolve condensed phase materials and often obfuscate the findings. More generally, conventional methods of explosives detection are ineffective at dealing with the problematic sample degradation properties of explosive materials.

To the contrary, according to aspects of the present disclosure, an explosives detection system and method are provided, which are highly reliable, and which provide high true positive and low false positive rates. The reliability is predicated at least in part, upon a first focused evaluation of for a specific explosive component (e.g., a nitrate) and then by independently collaborating the suggestion of the presence of an explosive by performing a second focused evaluation by detecting a secondary indicator of an explosive, such as a portion of a spectrum that is outside the bandwidth evaluated in the first focused evaluation. By properly setting the thresholds that are used to judge the presence of a signal at the focused evaluation range, a high confidence of true positive and low false positive rates is realized.

Moreover, because of the speed and capability of the system, implementations are available that can perform a detection before materials vaporize, thus creating the opportunity for collecting and preserving forensic evidence. In this regard, materials can be evaluated in particulate form.

Aspects of the present invention combine Raman spectroscopy, microscopic imaging, and software automation to analyze trace ($\geq 1$ picogram) materials. The systems can determine chemical composition, quantify particle size, characterize crystalline phase, etc. Moreover, the systems herein can be engineered or otherwise configured for specific missions (e.g., by specifying specific targets to evaluate, and/or by setting custom thresholds for those selected targets). Still further, the system can be constructed in a manner that is one-person portable (e.g., about 1.5 cubic feet), and which provide fully automated sample analysis utilizing optical analysis with no consumables.

Trace samples can diminish due to evaporation and chemical reactions. In this manner, the systems and methods herein can be used to monitor the rate of loss and reaction products of collected samples. The collected information can be used to provide recommendations for minimizing sample loss. The systems herein may also be configured to measure the crystal phase in sample, and determine its potential value as a forensic signature.

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be written in any combination of one or more programming languages, and may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. Aspects of the invention were chosen and described in order to best explain the principles of the invention and the practical application, and to enable others of ordinary skill in the art to understand the invention for various embodiments with various modifications as are suited to the particular use contemplated.

What is claimed is:

1. A method for detecting threat materials used in explosives, comprising:
   receiving a sample;
   selecting a target location within the sample that distinguishes a target material from an innocuous material;
   interrogating the selected target material, with a Raman laser, thereby producing a Raman spectrum;
   determining whether the interrogated target material is suspected of being a threat material by comparing an amplitude of a first spectral region in the Raman spectrum, to a first predetermined threshold;
   performing a verification, only when the determination indicates that the interrogated target material is suspected of being the threat material, by comparing a second predetermined threshold against an amplitude of a second spectral region in the Raman spectrum measured during the interrogation, where the second spectral region is different from the first spectral region; and
   activating an indicator if the verification indicates that the interrogated target material is the threat material.

2. The method of claim 1 further comprising:
   selecting a first spectral region to be narrow region that is sufficiently small to capture a single feature;
   wherein:
   interrogating the selected target material, with a Raman laser, thereby producing a Raman spectrum comprises:
      considering only the first spectral region when determining whether the interrogated target material is suspected of being a threat material.

3. The method of claim 1 further comprising predetermining that the threat material is a nitrate.

4. The method of claim 3, wherein:
   interrogating the selected target material, with a Raman laser further comprises:
      interrogating at least a portion of the Raman spectrum in the first spectral region, which is set to a wave number shift around 1050 cm$^{-1}$.

5. The method of claim 4, wherein:
   determining whether the interrogated target material is suspected of being a threat material by comparing an amplitude of a first spectral region in the Raman spectrum, to a first predetermined threshold comprises:
      comparing the amplitude of the measured portion of the Raman spectrum at approximately 1050 cm$^{-1}$ to the predetermined threshold, where the predetermined threshold is set to a value corresponding to a feature in the first spectral range that is indicative of a nitrate.

6. The method of claim 5, wherein:
   performing a verification, only when the determination indicates that the interrogated target material is suspected of being the threat material comprises:
      interrogating at least a portion of the Raman spectrum measured in the second spectral region, which is set to a wave number shift around 3225 cm$^{-1}$; and
   comparing a second predetermined threshold against an amplitude of a second spectral region in the Raman spectrum measured during the interrogation, which where the second spectral region is different from the first spectral region comprises:
      determining if the sample includes ammonium nitrate by comparing the amplitude of the measured portion of the Raman spectrum at approximately 3225 cm$^{-1}$ to the predetermined threshold, where the second threshold is set to a value corresponding to a feature in the second spectral range indicative of ammonium nitrate.

7. The method of claim 5, wherein:
   performing a verification, only when the determination indicates that the interrogated target material is suspected of being the threat material comprises:
      interrogating at least a portion of the Raman spectrum measured in the second spectral region, which is set to a wave number shift around 550 cm$^{-1}$; and
   comparing a second predetermined threshold against an amplitude of a second spectral region in the Raman spectrum measured during the interrogation, which where the second spectral region is different from the first spectral region comprises:
      determining if the sample includes urea nitrate by comparing the amplitude of the measured portion of the Raman spectrum at approximately 550 cm$^{-1}$ to the predetermined threshold, where the second threshold is set to a value corresponding to a feature in the second spectral range indicative of urea nitrate.

8. The method of claim 1, wherein:
   interrogating the selected target material, with a Raman laser, thereby producing a Raman spectrum, comprises:
      using interferometric spectroscopy to interrogate at least a portion of the selected target material to produce a spectrum of the portion of the selected target material.

9. The method of claim 1, wherein:
   interrogating the selected target material, with a Raman laser, thereby producing a Raman spectrum, comprises:
      interrogating at least a portion of the sample itself independently of reacted material.

10. The method of claim 1 further comprising detecting crystalline phases of the sample to determine a process of how the sample was created.

11. The method of claim 1, wherein receiving a sample further comprises receiving the sample onto a sample substrate in an open environment.

12. The method of claim 1, wherein receiving a sample further comprises drawing in a fluid stream, which is impacted onto a sample substrate to create the sample.

13. The method of claim 12, wherein receiving a sample further comprises at least one of using a pre-impactor to filter particulates in the fluid stream to a generally predetermined size, and impacting the fluid stream onto a gold sample substrate to create the sample.

14. The method of claim 1, wherein:
selecting a target location within the sample that distinguishes a target material from an innocuous material, comprises:
using a fluorescent device to select a target location by identifying a fluorescing region of the sample.

15. The method of claim 1 further comprising:
outputting an indication of the source of an explosive if threat material indicative of the explosive is detected.

16. The method of claim 15, wherein outputting an indication of the source of an explosive comprises determining at least one of the process and materials used to make the explosive and outputting determination results.

17. The method of claim 1, wherein receiving a sample comprises receiving the sample without perturbing the native state of an explosive being sampled.

18. A system for detecting threat materials used in explosives, comprising:
a sample collector that collects a sample;
a sample stage that receives the sample from the sample collector;
an interrogation station that includes a Raman laser source; and
a processor coupled to memory, where the processor is programmed to interact with the interrogation station to interrogate the sample and select a target location within the sample that distinguishes a target material from an innocuous material;
wherein the processor is further programmed to interact with the interrogation station to:
interrogate, with the Raman laser source, the target material, thereby producing a Raman spectrum;
determine whether the interrogated target material is suspected of being a threat material by comparing an amplitude of a first spectral region in the Raman spectrum, to a first predetermined threshold;
perform a verification, only when the determination indicates that the interrogated target material is suspected of being threat material, by comparing a second predetermined threshold against an amplitude of a second spectral region in the Raman spectrum measured during the interrogation, where the second spectral region is different from the first spectral region; and
activate an indicator if the verification indicates that the interrogated target material is the threat material.

* * * * *